United States Patent
Ishihara

(10) Patent No.: US 10,219,701 B2
(45) Date of Patent: Mar. 5, 2019

(54) FLUORESCENCE OBSERVATION APPARATUS

(71) Applicant: OLYMPUS CORPORATION, Tokyo (JP)

(72) Inventor: Yasushige Ishihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 769 days.

(21) Appl. No.: 14/865,499

(22) Filed: Sep. 25, 2015

(65) Prior Publication Data

US 2016/0007856 A1     Jan. 14, 2016

Related U.S. Application Data

(63) Continuation of application No. PCT/JP2014/055321, filed on Mar. 3, 2014.

(30) Foreign Application Priority Data

Mar. 29, 2013    (JP) ................................ 2013-073050

(51) Int. Cl.
    *A61B 6/00*          (2006.01)
    *A61B 5/00*          (2006.01)
                    (Continued)

(52) U.S. Cl.
    CPC .......... *A61B 5/0071* (2013.01); *A61B 1/0005* (2013.01); *A61B 1/00009* (2013.01);
                (Continued)

(58) Field of Classification Search
    CPC ... A61B 5/0071; A61B 1/00009; A61B 1/043; A61B 1/0638; A61B 1/0005
    See application file for complete search history.

(56) References Cited

U.S. PATENT DOCUMENTS

2013/0113908 A1     5/2013    Watanabe et al.

FOREIGN PATENT DOCUMENTS

EP        2384686 A1     11/2011
EP        2564755 A1      3/2013
            (Continued)

OTHER PUBLICATIONS

International Search Report dated May 20, 2014 issued in PCT/JP2014/055321.

(Continued)

*Primary Examiner* — Mallika D Fairchild
(74) *Attorney, Agent, or Firm* — Scully, Scott, Murphy & Presser, P.C.

(57) ABSTRACT

A fluorescence observation apparatus including a light source configured to irradiate an object with white light and excitation light; and a processor comprising hardware, wherein the processor is configured to implement: a fluorescence-image generating unit and a white-light-image generating unit configured to generate a fluorescence image G2 and a color white-light image, respectively; a condition setting unit configured to set weights individually for multiple color component images constituting the white-light image; and a combining unit configured to combine at least one color component image to which the fluorescence image has been added and the other color component images while applying the weights, and the condition setting unit configured to set the weights based on the color component images such that the weight for the color component image to which the fluorescence image is added is greater than the weights for the other color component images.

12 Claims, 8 Drawing Sheets

(51) Int. Cl.
  *A61B 1/00* (2006.01)
  *A61B 1/04* (2006.01)
  *G02B 23/24* (2006.01)
  *G06T 5/50* (2006.01)
  *A61B 1/06* (2006.01)

(52) U.S. Cl.
  CPC .......... *A61B 1/043* (2013.01); *G02B 23/2469* (2013.01); *G02B 23/2484* (2013.01); *G06T 5/50* (2013.01); *A61B 1/0638* (2013.01); *G06T 2207/10024* (2013.01); *G06T 2207/10064* (2013.01); *G06T 2207/20221* (2013.01); *G06T 2207/30004* (2013.01)

(56) References Cited

FOREIGN PATENT DOCUMENTS

| | | |
|---|---|---|
| EP | 2 589 328 A1 | 8/2013 |
| JP | H10-309282 A | 11/1998 |
| JP | 2005-204958 A | 8/2005 |
| JP | 2009-226072 A | 10/2009 |
| JP | 4533673 B2 | 9/2010 |
| JP | 2010-227254 A | 10/2010 |
| JP | 2012-147927 A | 8/2012 |
| JP | 2012-147935 A | 8/2012 |
| JP | 2013-039275 A | 2/2013 |
| WO | WO 2010/122884 A1 | 10/2010 |
| WO | WO 2011/135992 A1 | 11/2011 |
| WO | 2012/002320 A1 | 1/2012 |

OTHER PUBLICATIONS

European Extended Supplementary Search Report dated Nov. 14, 2016 received in European Patent Application No. 14 77 3962.7.

FLUORESCENCE OBSERVATION APPARATUS

CROSS-REFERENCE TO RELATED APPLICATIONS

This is a continuation of International Application PCT/JP2014/055321, with an international filing date of Mar. 3, 2014, which is hereby incorporated by reference herein in its entirety. This application claims the benefit of Japanese Patent Application No. 2013-073050, filed on Mar. 29, 2013, the content of which is incorporated herein by reference.

TECHNICAL FIELD

The present invention relates to fluorescence observation apparatuses.

BACKGROUND ART

In the related art, there are known fluorescence observation apparatuses of the type that acquires a white-light image representing the shape of biological tissue and a fluorescence image representing fluorescence from a lesion and that displays a fluorescence region in the fluorescence image as superimposed on the white-light image (e.g., see Patent Literature 1 and Patent Literature 2). With such an apparatus, since the lesion is displayed as the fluorescence region on the white-light image, it is possible to readily ascertain the positional relationship between the tissue and the lesion.

Specifically, according to Patent Literature 1, the gradation values of a fluorescence image are assigned to one of a red component image, a green component image, and a blue component image constituting a color white-light image, whereby the fluorescence region is displayed as a red, green, or blue region on the white-light image. In this case, in the region where the fluorescence region is superimposed, the white-light image contains information about the original gradation values, i.e., information about the shape of the tissue, which provides the advantage that it is possible to observe the shape of the tissue. According to Patent Literature 2, the fluorescence region in the white-light image is painted using pseudo-colors. In this case, the visibility of the fluorescence region is improved.

CITATION LIST

{PTL 1}
The Publication of Japanese Patent No. 4533673
{PTL 2}
Japanese Unexamined Patent Application, Publication No. 2005-204958

SUMMARY OF INVENTION

The present invention provides a fluorescence observation apparatus including a light source configured to irradiate an object with white light and excitation light; and a processor comprising hardware, wherein the processor is configured to implement: a fluorescence-image generating unit configured to generate a fluorescence image based on captured fluorescence generated at the object due to irradiation with the excitation light from the light source; a white-light-image generating unit configured to generate a color white-light image based on captured return light returned from the object due to irradiation with the white light from the light source; a condition setting unit configured to set weights individually for multiple color component images constituting the white-light image; and a combining unit configured to add the fluorescence image to at least one of the multiple color component images and combine the color component image to which the fluorescence image has been added and the other color component images while applying the weights that have been set by the condition setting unit, wherein the condition setting unit configured to set the weights based on the color component images of the white-light image and set the weights for the multiple color component images such that the weight for the color component image to which the fluorescence image is added is greater than the weights for the other color component images.

DESCRIPTION OF EMBODIMENTS

First Embodiment

Now, a fluorescence observation apparatus 1 according to a first embodiment of the present invention will be described with reference to FIGS. 1 and 2.

Figure 1:
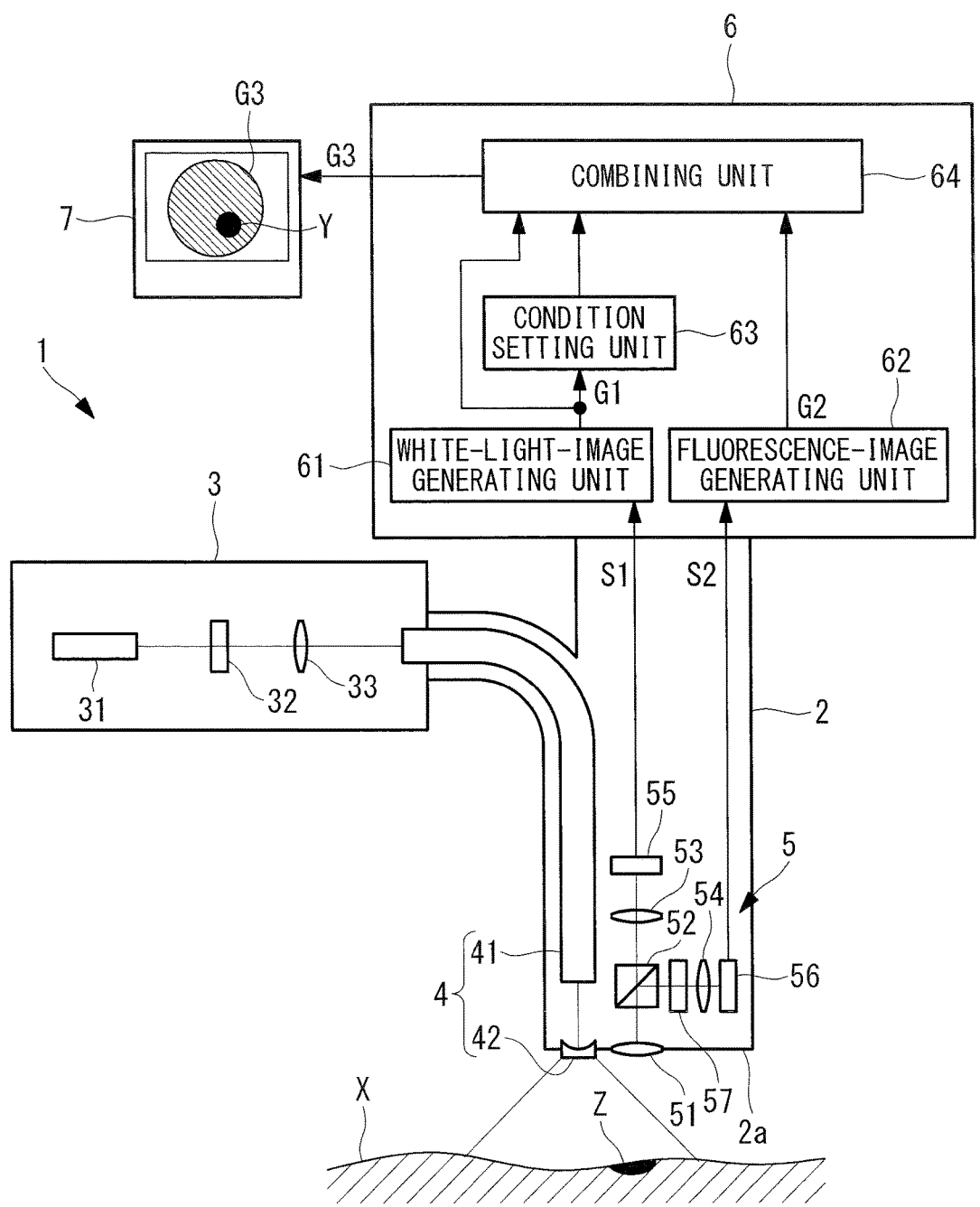
FIG. 1 is a diagram showing the overall configuration of a fluorescence observation apparatus according to a first embodiment of the present invention.

As shown in FIG. 1, the fluorescence observation apparatus 1 according to this embodiment, which is an endoscope device, includes a long, thin inserted portion 2 that is inserted into a body, a light source 3, an illumination unit 4 that radiates excitation light and white light (reference light) coming from the light source 3 toward an object X from the distal end 2a of the inserted portion 2, an image capturing unit 5 that is provided at the distal end 2a of the inserted portion 2 and that acquires image information S1 and S2 of the object X, an image processing unit 6 that is disposed at the proximal end of the inserted portion 2 and that processes the image information S1 and S2 acquired by the image capturing unit 5, and a display unit 7 that displays an image G3 that has been processed by the image processing unit 6.

The light source 3 includes a xenon lamp 31, a filter 32 that extracts excitation light and white light from light emitted from the xenon lamp 31, and a coupling lens 33 that focuses the excitation light and white light extracted by the filter 32. The filter 32 selectively transmits light in a wavelength band from 400 nm to 740 nm, which corresponds to the excitation light and white light. That is, in this embodiment, near-infrared light (e.g., a wavelength band from 700 nm to 740 nm) is used as the excitation light.

The illumination unit 4 includes a light guide fiber 41 that is disposed substantially along the full length of the inserted portion 2 in the lengthwise direction and also includes an illumination optical system 42 that is provided at the distal end 2a of the inserted portion 2. The light guide fiber 41 guides the excitation light and white light focused by the coupling lens 33. The illumination optical system 42 spreads out the excitation light and white light that have been guided by the light guide fiber 41 to irradiate the object X facing the distal end 2a of the inserted portion 2.

The image capturing unit 5 includes an objective lens 51 that collects light from the object X, a dichroic mirror 52 that reflects excitation light and fluorescence in the light collected by the objective lens 51 and that transmits white light (a wavelength band from 400 nm to 700 nm, return light) having shorter wavelengths than the excitation light, two focusing lenses 53 and 54 that focus the fluorescence reflected by the dichroic mirror 52 and the white light transmitted through the dichroic mirror 52, respectively, an image capturing element 55, such as a color CCD, that captures the white light focused by the focusing lens 54, and an image capturing element 56, such as a highly sensitive monochrome CCD or a color CMOS, that captures the fluorescence focused by the focusing lens 53. In the figure, the reference sign 57 denotes an excitation-light cutting filter that selectively transmits only the fluorescence (e.g., in the wavelength band of 760 nm to 850 nm) in the light reflected by the dichroic mirror 52, while blocking the excitation light.

As the image capturing element 56, in order to observe very weak fluorescence, a special image capturing element that can provide even higher sensitivity, such as an EMCCD (electron multiplier CCD) or an ICCD (image intensifier CCD), may be used. Alternatively, image capturing with high sensitivity may be realized by using a monochrome CCD by executing binning processing to add up gradation values of multiple pixels within the element.

With the combination of the filter 32, the dichroic mirror 52, and the excitation-light cutting filter 57 having the wavelength characteristics described above, for example, it is possible to simultaneously acquire a white-light image G1 and a fluorescence image G2, which will be described later, by observing the result of administering the object X with a drug (Anti-CEA-Cy7) in which an antibody (Anti-CEA antibody) against CEA (Carcinoembryonic antigen) is marked with a fluorescent dye Cy 7 (from GE Healthcare). CEA is a protein that is known to be expressed specifically in cancer. This makes it possible to acquire an image of a cancer lesion as a fluorescence image G2.

The image processing unit 6 includes a white-light-image generating unit 61 that generates a white-light image G1 from white-light-image information S1 acquired by the image capturing element 55, a fluorescence-image generating unit 62 that generates a fluorescence image G2 from fluorescence-image information S2 acquired by the image capturing element 56, a condition setting unit 63 that sets weights for the individual color-component images constituting the white-light image G1, and a combining unit 64 that adds the fluorescence image G2 to one of the color-component images of the white-light image G1 to generate a combined image G3.

The image processing unit 6 is a computer including a central processing unit (CPU), a main storage device such as RAM (Random Access Memory), and an auxiliary storage device. The auxiliary storage device is a non-transitory computer-readable storage medium such as an optical disc or a magnetic disk, and stores an image processing program. The CPU loads the image processing program stored in the auxiliary storage device into the main storage device, and then executes the program, thereby to implement the functions of the white-light-image generating unit 61, the fluorescence-image generating unit 62, the condition setting unit 63, and the combining unit 64. Alternatively, the functions of those units 61, 62, 63, and 64 may be implemented by dedicated hardware such as ASIC (Application Specific Integrated Circuit).

Eq. (1) below expresses the generalized relationships between the three color-component images constituting the white-light image G1 and the three color-component images constituting the combined image G3. In Eq. (1), R', G', and B' denote the gradation values of the red (R) component, the green (G) component, and the blue (B) component of the individual pixels of the combined image G3, R, G, and B denote the gradation values of the R component, the G component, and the B component of the individual pixels of the white-light image G1, F denotes the gradation values of the individual pixels of the fluorescence image G2, r, g, and b denote coefficients, and $S_R$, $S_G$, and $S_B$ denote thresholds for the gradation values F. When F≤Si (where i=r, g, b), F−Si=0. Furthermore, in the case where any one of R', G', and B' becomes less than zero by calculating Eq. 1, the value is set to zero.

[Eq. 1]

$$R'(x,y)=R(x,y)+r(x,y)\times(F(x,y)-S_R(x,y))$$

$$G'(x,y)=G(x,y)+g(x,y)\times(F(x,y)-S_G(x,y))$$

$$B'(x,y)=B(x,y)+b(x,y)\times(F(x,y)-S_B(x,y)) \quad (1)$$

Here, x and y denote coordinates corresponding to positions in the white-light image G1 and the fluorescence image G2. Furthermore, although each variable is a value set for each coordinate (x, y) also in Eqs. (2) to (18) given below, the notation (x, y) is omitted in order to avoid making the equations complex. For example, R(x, y) and F(x, y) are simply expressed as R and F.

In this embodiment, since the color of the biological tissue serving as the object X contains a high level of R components, green is preferable as the display color of the fluorescence region Y in the combined image G3. Thus, preferably, weighting should be applied such that the G component image of the white-light image G1 corresponding to the fluorescence region Y will be emphasized, thereby generating an image in which the contrast in green is emphasized between the fluorescence region Y and the other region in the combined image G3.

Thus, the following description will be given in the context of an example where the combined image G3 is generated such that the G component of the white-light image G1 corresponding to the fluorescence region Y will be emphasized.

The combining unit 64 compares the gradation values of the individual pixels of the fluorescence image G2 with the threshold $S_G$ and adds the fluorescence region Y having gradation values F greater than the threshold $S_G$ to the G component image of the white-light image G1. By doing so, it is possible to remove weak fluorescence or noise from the fluorescence image G2 and to selectively extract and display a lesion as a fluorescence region Y in the combined image G3.

Furthermore, in generating the combined image G3, for the R component and B component of the white-light image G1, preferably, the gradation values F of the individual pixels of the fluorescence image G2 should be compared with the thresholds $S_R$ and $S_B$ to extract a region having gradation values F greater than the thresholds $S_R$ and $S_B$, applying negative weights to the extracted regions. The weights are determined according to the coefficients r, g, and b and the thresholds $S_R$, $S_G$, and $S_B$, and these coefficients and thresholds are set by the condition setting unit 63.

As described above, in generating the combined image G3, preferably, for the gradation values of the white-light image G1 containing a high level of R components, values determined according to the gradation values F of the fluorescence region Y of the fluorescence image G2, the coefficient g, and the threshold $S_G$ are added to the gradation values of the G component of the white-light image G1, and values determined according to the gradation values F of the fluorescence image G2, the coefficients r and b, and the thresholds $S_R$ and $S_B$ are subtracted from the gradation values of the R component and the B component of the white-light image G1.

The combining unit 64 and the condition setting unit 63 execute processing by using the coefficients r, g, and b and the thresholds $S_R$, $S_G$, and $S_B$ that are set according to Eq. (2) below. That is, the condition setting unit 63 sets smaller values for the thresholds $S_R$ and $S_B$ as the R component and the B component become greater. Accordingly, the combining unit 64 generates the combined image G3 by using an R component image and a B component image in which gradation values are partially reduced in the regions that are substantially the same as the fluorescence region Y.

[Eq. 2]

$$S_R = 1000 + 1000 \times \frac{4095 - R}{4095}$$
$$S_G = 1000$$
$$S_B = 1000 + 1000 \times \frac{4095 - B}{4095}$$
$$r = -1$$
$$g = 1$$
$$b = -1$$

(2)

In Eq. (2), the dynamic range of the individual images G1, G2, and G3 is assumed to be 12 bits. That is, the individual gradation values R, G, B, R', G', B', and F are represented by numerals in the range of 0 to 4095, and the thresholds $S_R$ and $S_B$ vary from 1000 to 2000, depending on the gradation values R or B.

Next, the operation of the thus-configured fluorescence observation apparatus 1 will be described.

In order to observe biological tissue inside a body, serving as the object X, by using the fluorescence observation apparatus 1 according to this embodiment, a fluorescent material that accumulates at a lesion Z is administered to the object X in advance. Then, the inserted portion 2 is inserted into the body and the distal end 2a thereof is placed so as to face the object X, and excitation light and white light are radiated toward the object X from the distal end 2a of the inserted portion 2 by the operation of the light source 3.

At the object X, the fluorescent material contained in the lesion Z is excited by the excitation light, whereby fluorescence is emitted, and white light is reflected at the surface of the object X. Parts of the fluorescence emitted from the object X and the reflected white light return to the distal end 2a of the inserted portion 2 and are collected by the objective lens 51.

Of the light collected by the objective lens 51, the white light is transmitted through the dichroic mirror 52, is focused by the focusing lens 54, and is acquired by the image capturing element 55 as white-light-image information S1. On the other hand, the fluorescence collected by the objective lens 51 is reflected by the dichroic mirror 52, and after the excitation light is removed by the excitation-light cutting filter 57, the reflected fluorescence is focused by the focusing lens 53 and is acquired by the image capturing element 56 as fluorescence-image information S2. The image information S1 and S2 acquired by the individual image capturing elements 55 and 56 is forwarded to the image processing unit 6.

Figure 2:
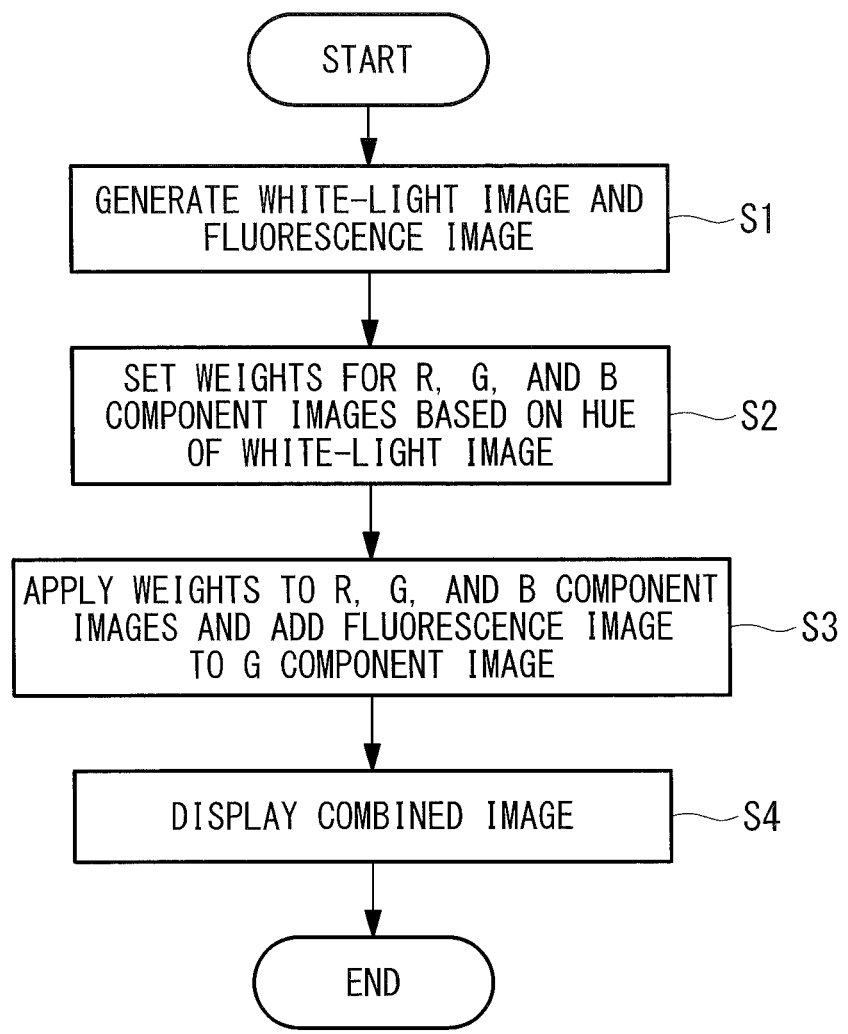
FIG. 2 is a flowchart for explaining processing executed by an image processing unit shown in FIG. 1.

FIG. 2 shows a flowchart for explaining image processing by the image processing unit 6.

In the image processing unit 6, the white-light-image information S1 is input to the white-light-image generating unit 61 to generate a white-light image G1, and the fluorescence-image information S2 is input to the fluorescence-image generating unit 62 to generate a fluorescence image G2 (step S1). The white-light image G1 is forwarded to the condition setting unit 63 and the combining unit 64, and the fluorescence image G2 is forwarded to the combining unit 64.

In the combining unit 64, a fluorescence region Y having gradation values greater than or equal to a predetermined threshold $S_G$ in the fluorescence image G2 is assigned to the G component image of the white-light image G1, whereby a combined image G3 in which the fluorescence region Y is displayed in green is generated (step S3), and the generated combined image G3 is displayed on the display unit 7 (step S4).

Here, the condition setting unit 63 sets thresholds $S_R$ and $S_B$ based on the color components of the individual pixels of the white-light image G1 (step S2), and the thresholds $S_R$ and $S_B$ that have been set are forwarded to the combining unit 64. In the combining unit 64, regions that are substantially the same as the fluorescence region Y are extracted from the R component image and the B component image of the white-light image G1 based on the thresholds $S_R$ and $S_B$, the gradation values are reduced by applying negative weights based on the color components and the gradation values F of the extracted regions, and the result is used for generating the combined image G3.

As described above, according to this embodiment, in the fluorescence region Y of the combined image G3, as the redness and blueness of the object X serving as the background become stronger, the redness and blueness are suppressed more strongly, so that green, in which the fluorescence region Y is displayed, is emphasized relative to red and blue. This makes it possible to constantly display the fluorescence region Y representing the lesion Z in clear green that readily allows visual recognition. In particular, it is possible to emphasize green effectively by suppressing red, which is the complementary color of green. Furthermore, in the region except the fluorescence region Y of the combined image G3, it is possible to display the white-light image G1 as is, which represents a precise reproduction of information about the color and shape of the object X.

Although the thresholds $S_R$ and $S_B$ are varied depending on the color components of the white-light image G1 in this embodiment, alternatively, for example, coefficients r and b may be varied depending on the color components of the white-light image G1, as expressed in equation (3) below.

Also in this case, it is possible to attain a similar effect by adjusting the magnitudes of the negative weights that are applied to the R component image and the B component image.

[Eq. 3]

$$S_R = 1000$$
$$S_G = 1000$$
$$S_B = 1000$$
$$r = -1 \times \frac{R}{4095}$$
$$g = 1$$
$$b = -1 \times \frac{B}{4095}$$
(3)

Furthermore, in this embodiment, equations (2) and (3) may be combined to simultaneously vary both the thresholds $S_R$ and $S_B$ and the coefficients r and b.

Furthermore, although the dynamic range of gradation values is assumed to be 12 bits in this embodiment, without limitation to this dynamic range, for example, similar processing can be executed in the case of 8 bits or 16 bits. That is, in place of the constant 4095 in equations (2) and (3) given above, 255 should be used for 8 bits and 65535 should be used for 16 bits.

When the processing expressed in equation (2) above is executed, for example, assuming that the R, G, and B gradation values of the white-light image G1 at a certain coordinate position in the fluorescence region Y are (R, G, B)=(3000, 1000, 500) and the gradation value F of the fluorescence image G2 is 2000, then $(S_R, S_G, S_B)$=(1267, 1000, 1878), so that (R', G', B')=(2267, 2000, 377) . . . (A). That is, the gradation values of the G component of the white-light image G1 increase and the gradation values of the R component and B component of the white-light image G1 decrease in accordance with the gradation values of the fluorescence image G2, thereby obtaining a combined image G3 in which the G component is emphasized. Furthermore, since the gradation values of the R component and B component in the combined image G3 reflect the gradation values of the R component and B component in the white-light image G1, information about the shape of the object X also remains in the combined image G3.

On the other hand, assuming that the thresholds $S_R$ and $S_B$ are constant values that do not depend on the gradation values of the R component and B component of the white-light image G1 and that the values are 2000, which is the maximum value as defined in equation (2), then $(S_R, S_G, S_B)$=(2000, 1000, 2000), so that (R', G', B')=(3000, 2000, 500) . . . (B). Also in this case, the G component in the combined image G3 increases in accordance with the gradation values of the fluorescence image G2; however, since the R component and B component are strong relative to the G component, the visibility of the emphasized G component is inferior compared with (A).

On the other hand, assuming that the thresholds $S_R$ and $S_B$ are constant values that do not depend on the gradation values of the R component and B component of the white-light image G1 and that the values are 1000, which is the minimum value as defined in equation (2), then $(S_R, S_G, S_B)$=(1000, 1000, 1000), so that (R', G', B')=(2000, 2000, 0) . . . (C). In this case, since the gradation values of the G component are greater than the gradation values of the R and B components in the combined image G3, the visibility of the emphasized G component is superior compared with (A) and (B). However, the gradation values of the R component in the combined image G3 become lower compared with (A), and the B component of the combined image G3 becomes zero, so that information about the B component of the white-light image G1 becomes lost. Thus, the amount of information about the shape of the object X reflected in the combined image G3 is inferior compared with (A).

Therefore, in the case (A), where the values of the thresholds $S_R$, $S_G$, and $S_B$ are varied appropriately in accordance with the color components of the white-light image G1, compared with the cases (B) and (C), where the values of the thresholds $S_R$, $S_G$, and $S_B$ are always fixed, in the combined image G3, it is possible to provide a more appropriate image in which the visibility of the G component reflecting information about the fluorescence image G2 is ensured and in which information about the shape of the object X is maintained as much as possible.

Other embodiments and modifications described below also provide advantages similar to those described for this embodiment.

In the calculations described above, values below the decimal points are all rounded down.

Furthermore, although the coefficients r and b are negative values in this embodiment, the coefficients r and b may be positive or zero as long as these values satisfy the relationship g>r, b. It is possible to provide similar advantages also in this case.

Next, modifications of the processing by the condition setting unit 63 and the combining unit 64 will be described.

First Modification of the First Embodiment

In a first modification, instead of setting the negative weights for the R component image and B component image depending on the color components of the white-light image G1, the condition setting unit 63 sets a positive weight for the G component image depending on the color components of the white-light image G1.

Specifically, the condition setting unit 63 sets a smaller value for the threshold $S_G$ as the gradation values of the R component and B component of the white-light image G1 become greater, as expressed in equation (4) below.

This makes it possible to increase the gradation values that are added to the white-light image G1 for the fluorescence region Y, thereby emphasizing the green color in the fluorescence region Y in the combined image G3. Furthermore, the gradation values of the R component and B component decrease as the gradation values F increase in the fluorescence region Y of the combined image G3 according to equation (4), which makes it possible to emphasize the green color in the fluorescence region Y more effectively.

[Eq. 4]

$$S_R = 1000$$
$$S_G = 1000 + 500 \times \frac{4095 - R}{4095} + 500 \times \frac{4095 - B}{4095}$$
$$S_B = 1000$$
$$r = -1$$
$$g = 1$$
$$b = -1$$
(4)

In this modification, the coefficient g may be varied depending on the color components of the white-light image G1 as expressed in equation (5) below instead of equation (4).

[Eq. 5]

$$S_R = 1000 \\ S_G = 1000 \\ S_B = 1000 \\ r = -1 \\ g = 1 + 0.5 \times \frac{R}{4095} + 0.5 \times \frac{B}{4095} \\ b = -1 \quad (5)$$

Furthermore, in this modification, equations (2), (3), (4), and (5) may be used in arbitrary combinations. For example, as expressed in equation (6) below, the coefficients r, g, and b and the thresholds $S_R$, $S_G$, and $S_B$ may be varied simultaneously depending on the color components of the white-light image G1.

[Eq. 6]

$$S_R = 1000 + 1000 \times \frac{4095 - R}{4095} \\ S_G = 1000 + 500 \times \frac{4095 - R}{4095} + 500 \times \frac{4095 - B}{4095} \\ S_B = 1000 + 1000 \times \frac{4095 - B}{4095} \\ r = -1 \times \frac{R}{4095} \\ g = 1 + 0.5 \times \frac{R}{4095} + 0.5 \times \frac{B}{4095} \\ b = -1 \times \frac{B}{4095} \quad (6)$$

Second Modification of the First Embodiment

In a second modification, the condition setting unit 63 sets the coefficients r, g, and b and the thresholds $S_R$, $S_G$, and $S_B$ by using the ratio between the gradation values of the G component to be emphasized and the gradation values of the R component and B component to be reduced, as expressed in equation (7) below, instead of using the gradation values of the individual color components. $R_G$ and $B_G$ in equation (7) are defined by equation (8). $N_{RG}$ and $N_{BG}$ in equation (8) are defined by equation (9) below. Max[R/G] denotes the maximum value of R/G among all the pixels, and Max[B/G] denotes the maximum value of B/G among all the pixels.

Accordingly, weights are set based on the gradation values of the R component image and B component image relative to the gradation values of the G component image, so that it is possible to set weights for the individual color component images more suitably for the color components of the white-light image G1.

[Eq. 7]

$$S_R = 1000 + 1000 \times \frac{4095 - R_G}{4095} \quad (7) \\ S_G = 1000 + 500 \times \frac{4095 - R_G}{4095} + 500 \times \frac{4095 - B_G}{4095} \\ S_B = 1000 + 1000 \times \frac{4095 - B_G}{4095} \\ r = -1 \times \frac{R_G}{4095} \\ g = 1 + 0.5 \times \frac{R_G}{4095} + 0.5 \times \frac{B_G}{4095} \\ b = -1 \times \frac{B_G}{4095}$$

[Eq. 8]

$$R_G = 4095 \times \frac{1}{N_{RG}} \times \frac{R}{G} \quad (8) \\ B_B = 4095 \times \frac{1}{N_{BG}} \times \frac{B}{G}$$

[Eq. 9]

$$N_{RG} = \text{Max}\left[\frac{R}{G}\right] \quad (9) \\ N_{BG} = \text{Max}\left[\frac{B}{G}\right]$$

Third Modification of the First Embodiment

In a third modification, the condition setting unit 63 sets weights depending on the G component of the white-light image G1 instead of setting weights depending on the R component and B component of the white-light image G1.

Specifically, the condition setting unit 63 sets the coefficients r, g, and b and the thresholds $S_R$, $S_G$, and $S_B$ such that the positive weight for the G component image increases and the negative weights for the R component image and B component image increase as the gradation values of the G component decrease, as expressed in equation (10) below.

Also in this case, it is possible to effectively emphasize the green color in the fluorescence region Y of the combined image G3.

[Eq. 10]

$$S_R = 1000 + 1000 \times \frac{G}{4095} \quad (10) \\ S_G = 1000 + 1000 \times \frac{G}{4095} \\ S_B = 1000 + 1000 \times \frac{G}{4095} \\ r = -1 \times \frac{4095 - G}{4095} \\ g = 1 + 0.5 \times \frac{4095 - G}{4095} + 0.5 \times \frac{4095 - G}{4095} \\ b = -1 \times \frac{4095 - G}{4095}$$

Second Embodiment

Next, a fluorescence observation apparatus 100 according to a second embodiment of the present invention will be described.

Figure 3:
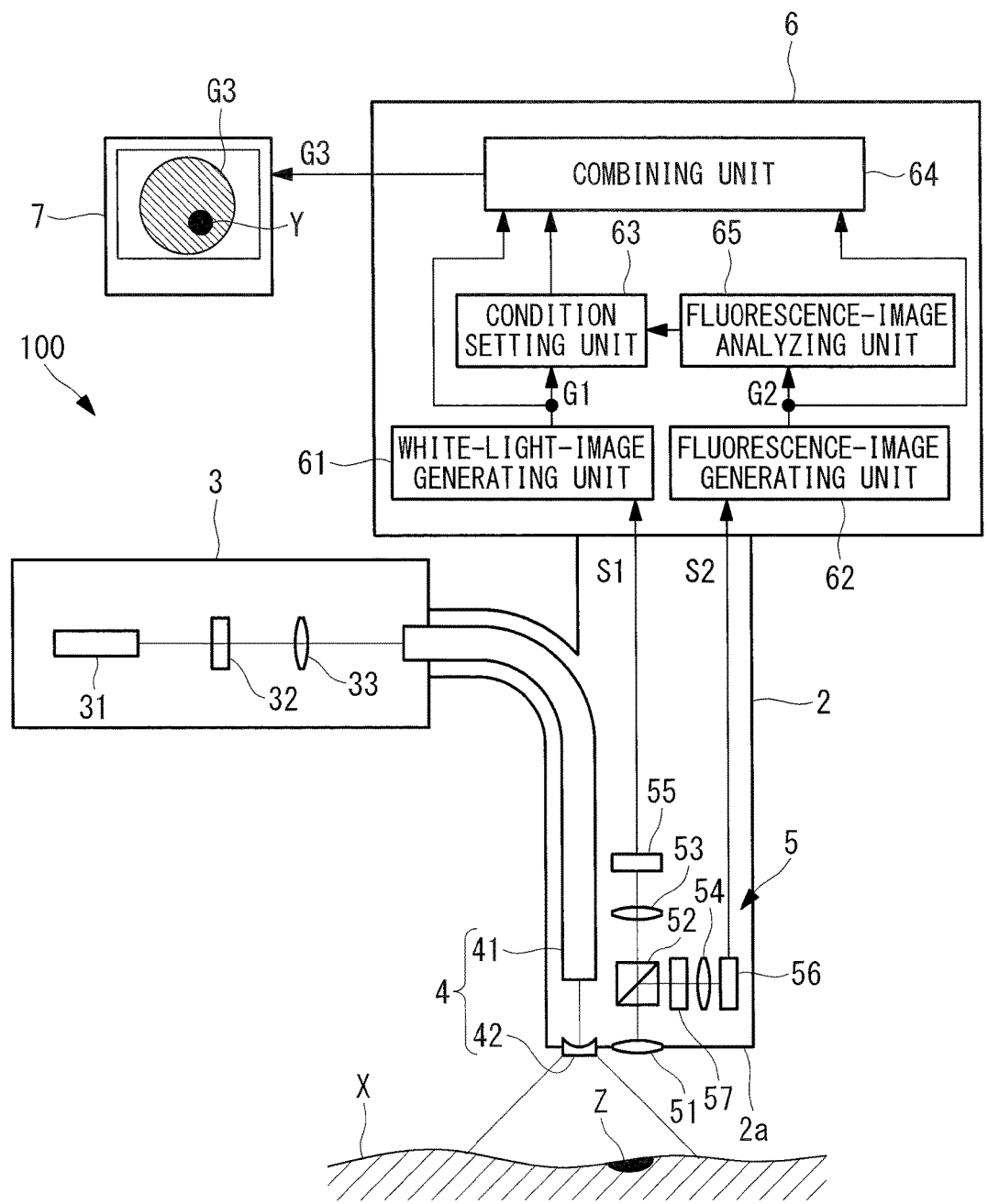
FIG. 3 is a diagram showing the overall configuration of a fluorescence observation apparatus according to a second embodiment of the present invention.

As shown in FIG. 3, the fluorescence observation apparatus 100 according to this embodiment differs from the first embodiment mainly in that the image processing unit 6 further includes a fluorescence-image analyzing unit 65 that calculates the average m and standard deviation σ a of the gradation values of the fluorescence image G2 from the distribution of the gradation values and in that the condition setting unit 63 sets the thresholds $S_R$, $S_B$, and $S_G$ by using the average m and standard deviation σ calculated by the fluorescence-image analyzing unit 65. Thus, regarding this embodiment, the description will be directed mainly to the fluorescence-image analyzing unit 65 and the condition setting unit 63, and parts that are common to those in the first embodiment will be designated by the same reference signs and will not be described.

The fluorescence-image analyzing unit 65 is implemented by the computer or the dedicated hardware.

The fluorescence-image analyzing unit 65 calculates the distribution of gradation values of the entirety of the fluorescence image G2 or a predetermined portion thereof constituting a region of interest (ROI), calculates the average m and standard deviation σ of the gradation values of the fluorescence image G2 from the calculated distribution, and outputs the obtained average m and standard deviation σ to the condition setting unit 63.

The condition setting unit 63 calculates the thresholds $S_R$, $S_B$, and $S_G$ from the sum of the average m and standard deviation σ of the gradation values, input from the fluorescence-image analyzing unit 65, as expressed in equation (11) below. Here, ci and di (where i=r, g, b) denote coefficients that vary depending on the gradation values of the R component and the gradation values of the B component and are defined by equation (12) below.

[Eq. 11]

$$S_R = c_R m + d_R \sigma \quad (11)$$
$$S_G = c_G m + d_G \sigma$$
$$S_B = c_B m + d_B \sigma$$
$$r = -1$$
$$g = 1$$
$$b = -1$$

[Eq. 12]

$$c_R = 0.5 + 1 \times \frac{4095 - R}{4095} \quad (12)$$
$$d_R = 1 + 0.5 \times \frac{4095 - R}{4095}$$
$$c_G = 1$$
$$d_G = 1$$
$$c_B = 0.5 + 1 \times \frac{4095 - B}{4095}$$
$$d_B = 1 + 0.5 \times \frac{4095 - B}{4095}$$

In equation (12), coefficients $c_R$ and $c_B$ vary from 0.5 to 1.5, and they decrease as the gradation values of the R component and B component increase. Coefficients $d_R$ and $d_B$ vary from 1 to 1.5, and they decrease as the gradation values of the R component and B component increase. Thus, as the redness and blueness of the white-light image G1 increase, the thresholds $S_R$ and $S_B$ decrease, and the negative weights for the R component image and B component image increase.

Next, the operation of the thus-configured fluorescence observation apparatus 100 will be described.

Figure 4:
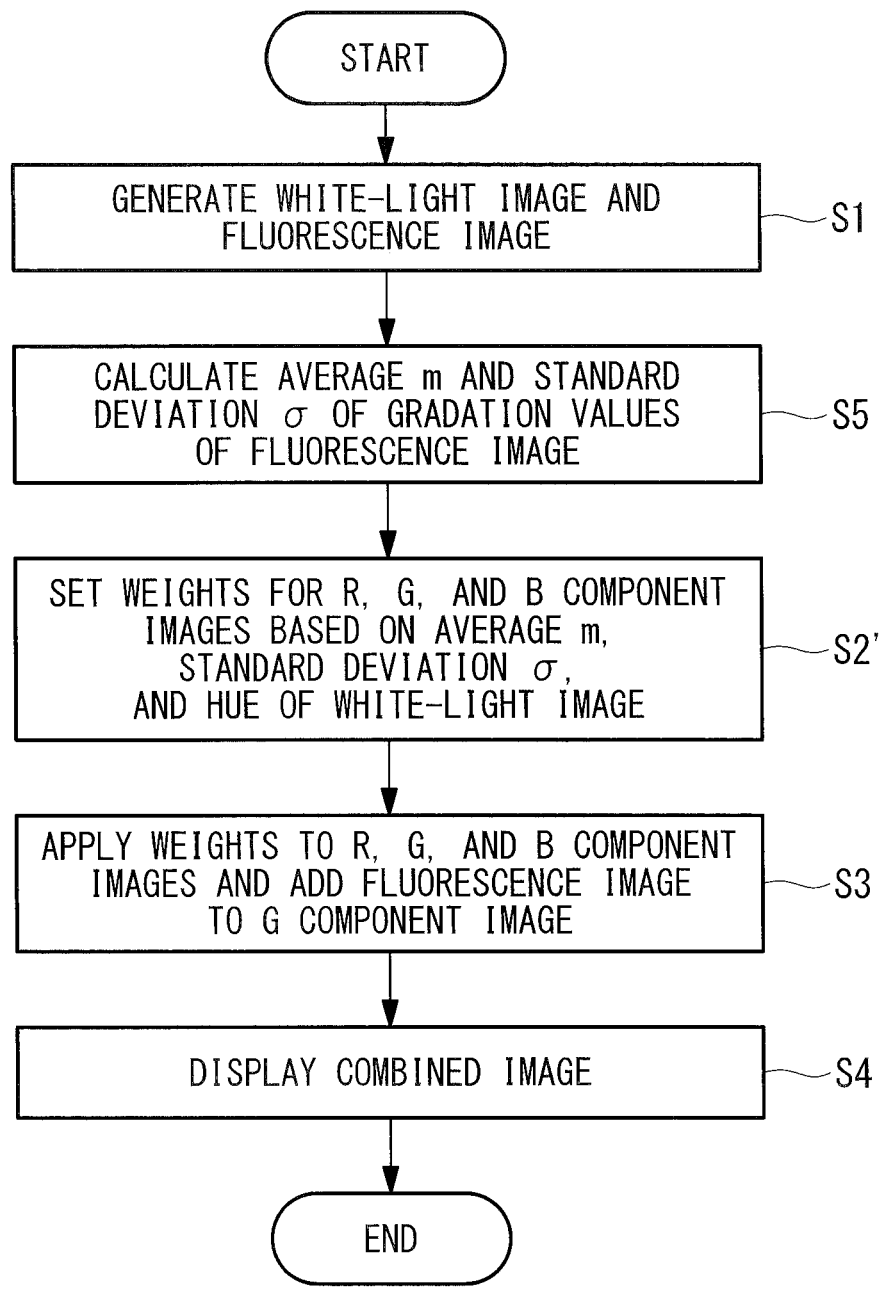
FIG. 4 is a flowchart for explaining processing executed by an image processing unit shown in FIG. 3.

With the fluorescence observation apparatus 100 according to this embodiment, processing is executed in the same manner as in the first embodiment until the generation of the white-light image G1 and the fluorescence image G2 (step S1). The generated fluorescence image G2 is forwarded to the fluorescence-image analyzing unit 65. As shown in FIG. 4, the fluorescence-image analyzing unit 65 calculates the distribution of the gradation values F of the fluorescence image G2 and calculates the average m and standard deviation σ of the gradation values F from the distribution (step S5). Then, the condition setting unit 63 sets the thresholds $S_R$, $S_G$, and $S_B$ by using the average m and standard deviation σ (step S2'). In step S3, a combined image G3 is generated based on equation (1) by using the thresholds $S_R$, $S_G$, and $S_B$ set in step S2'.

Figure 5:
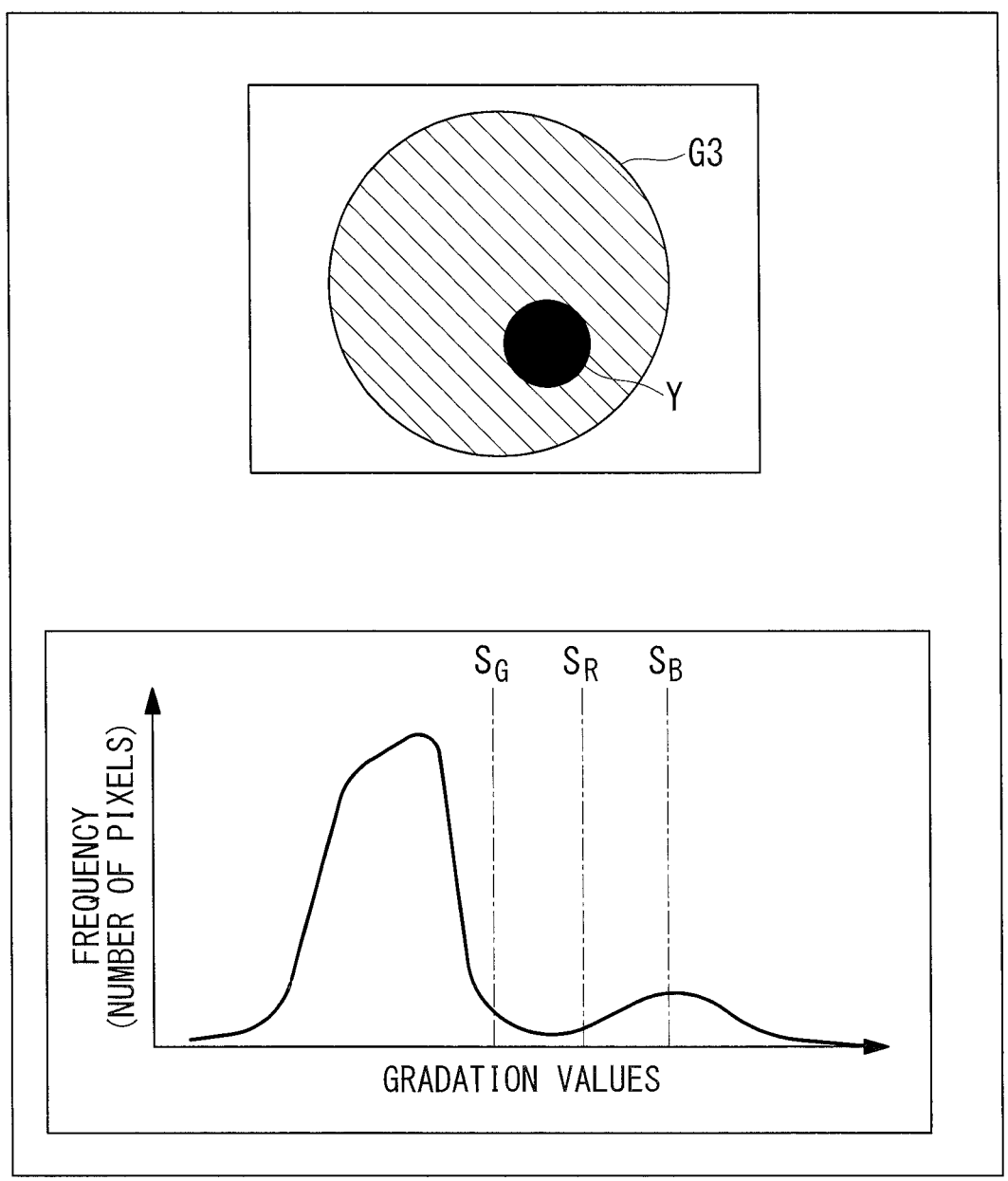
FIG. 5 is a diagram showing an example of display on a display unit of the fluorescence observation apparatus shown in FIG. 3.

FIG. 5 shows an example of display by the display unit 7 according to this embodiment, in which the combined image G3 (upper) and a histogram of the gradation values F of the fluorescence image G2 (lower) are shown. The histogram shows the thresholds $S_R$, $S_G$, and $S_B$. The thresholds $S_R$, $S_G$, and $S_B$ that are calculated based on the average m and standard deviation σ vary in accordance with variations in the distribution of the gradation values F, and the thresholds $S_R$, $S_G$, and $S_B$ increase as the brightness of the fluorescence image G2 as a whole increases.

As described above, according to this embodiment, the thresholds $S_R$, $S_G$, and $S_B$ vary depending on changes in the gradation values of the fluorescence image G2 as a whole as well as the color components of the white-light image G1. Thus, when the brightness of the fluorescence image G2 as a whole changes due to a change in observation conditions, such as the observation distance, observation angle, etc. between the distal end 2a of the inserted portion 2 and the object X, the thresholds $S_R$, $S_G$, and $S_B$ are also changed to more suitable values. Accordingly, the fluorescence region Y is extracted from the fluorescence image G2 more accurately, and the magnitudes of the negative weights that are applied to the R component image and B component image are set more appropriately. Therefore, it becomes possible to display the fluorescence region Y more accurately in the combined image G3 and to emphasize the fluorescence region Y more appropriately.

Although processing for emphasizing the G component in accordance with the gradation values of the fluorescence image G2 has been described in the context of this embodiment, methods similar to the method described in the context of this embodiment can be used also in cases where the R component or B component is to be emphasized.

Modification of the Second Embodiment

Next, a modification of the processing by the condition setting unit 63 and the combining unit 64 according to this embodiment will be described.

In this modification, the condition setting unit 63 sets positive weights for the G component image depending on the color components of the white-light image G1 instead of setting negative weights for the R component image and B component image depending on the color components of the white-light image G1.

Specifically, the condition setting unit 63 sets small values for the coefficients $c_G$ and $d_G$ such that the threshold $S_G$ decreases as the gradation values of the R component and B component in the white-light image G1 increase, as expressed in equation (13) below.

Accordingly, it is possible to emphasize the green color of the fluorescence region Y in the combined image G3 by increasing the gradation values that are added for the fluorescence region Y in the white-light image G1. Furthermore, since the R component and B component are suppressed in the fluorescence region Y of the combined image G3 according to equation (13), it is possible to emphasize the green color in the fluorescence region Y more effectively.

[Eq. 13]

$$c_R = 1$$
$$d_R = 1$$
$$c_G = 0.5 + 0.5 \times \frac{4095 - R}{4095} + 0.5 \times \frac{4095 - B}{4095}$$
$$d_G = 1 + 0.25 \times \frac{4095 - R}{4095} + 0.25 \times \frac{4095 - B}{4095}$$
$$c_B = 1$$
$$d_B = 1$$
(13)

In this modification, equations (12) and (13) may be combined such that the condition setting unit 63 simultaneously varies the coefficients $c_R$, $c_G$, $c_B$, $d_R$, $d_G$, and $d_B$ depending on the color components of the white-light image G1, as expressed in equation (14) below.

This makes it possible to emphasize the green color in the fluorescence region Y more effectively.

[Eq. 14]

$$c_R = 0.5 + 1 \times \frac{4095 - R}{4095}$$
$$d_R = 1 + 0.5 \times \frac{4095 - R}{4095}$$
$$c_G = 0.5 + 0.5 \times \frac{4095 - R}{4095} + 0.5 \times \frac{4095 - B}{4095}$$
$$d_G = 1 + 0.25 \times \frac{4095 - R}{4095} + 0.25 \times \frac{4095 - B}{4095}$$
$$c_B = 0.5 + 1 \times \frac{4095 - B}{4095}$$
$$d_B = 1 + 0.5 \times \frac{4095 - B}{4095}$$
(14)

Third Embodiment

Next, a fluorescence observation apparatus 200 according to a third embodiment of the present invention will be described.

Figure 6:
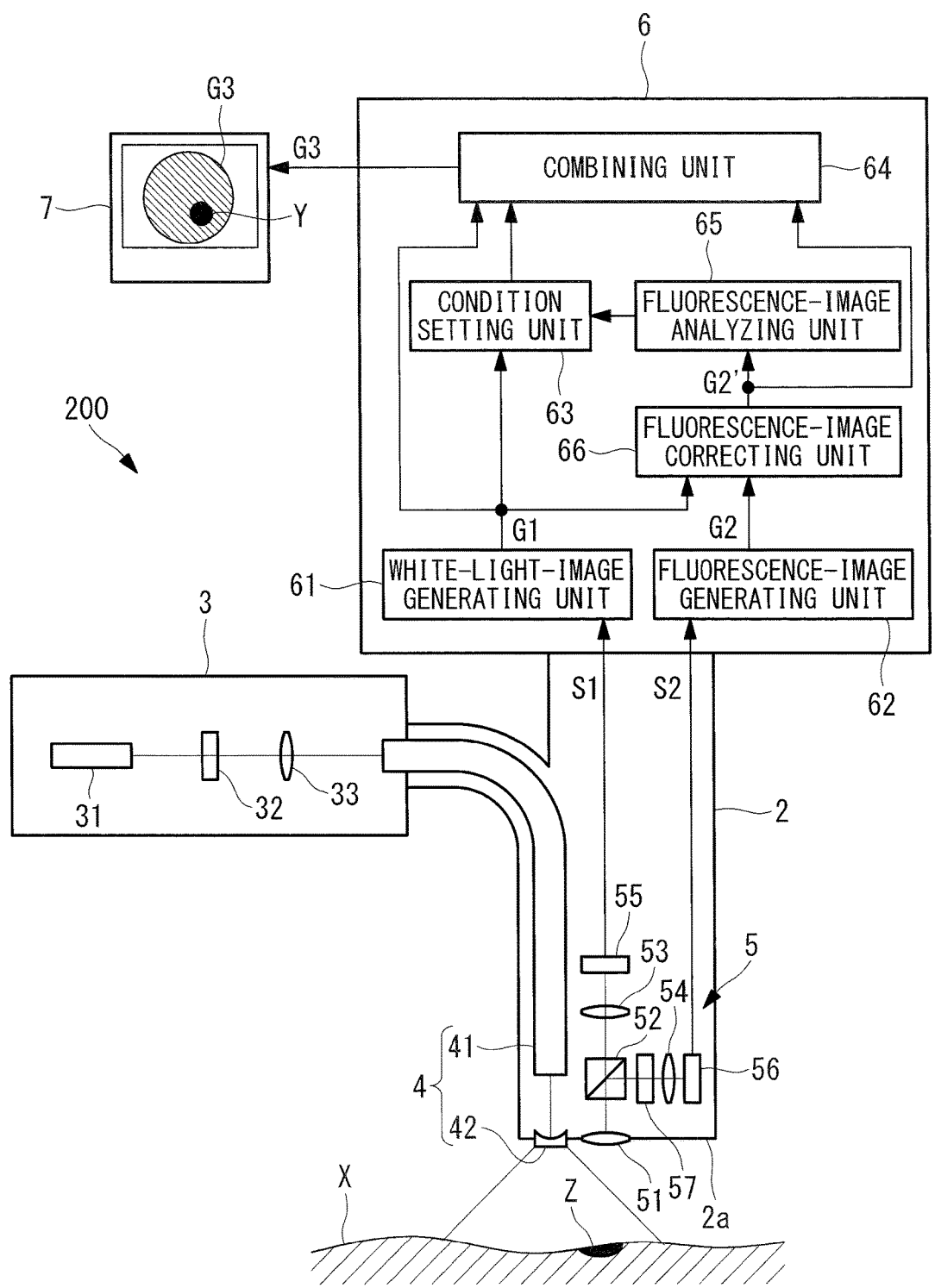
FIG. 6 is a diagram showing the overall configuration of a fluorescence observation apparatus according to a third embodiment of the present invention.

The fluorescence observation apparatus 200 according to this embodiment is a modification of the fluorescence observation apparatus 100 according to the second embodiment. As shown in FIG. 6, the third embodiment differs from the second embodiment mainly in that the image processing unit 6 further includes a fluorescence-image correcting unit 66 that corrects the gradation values of the fluorescence image G2 by using the white-light image G1 and in that the fluorescence-image analyzing unit 65 calculates the average m' and standard deviation σ' by using the fluorescence image G2' that has been corrected by the fluorescence-image correcting unit 66. Thus, regarding this embodiment, the description will be directed mainly to the fluorescence-image correcting unit 66 and the fluorescence-image analyzing unit 65, and parts common to those in the first and second embodiments will not be described.

The fluorescence-image correcting unit 66 is implemented by the computer or the dedicated hardware.

The fluorescence-image correcting unit 66 divides the gradation values of the individual pixels of the fluorescence image G2, input from the fluorescence-image generating unit 62, by the gradation values of the individual pixels of the white-light image G1, input from the white-light-image generating unit 61, thereby generating a fluorescence image G2' in which the gradation values have been corrected (hereinafter referred to as a corrected fluorescence image), and outputs the corrected fluorescence image G2' that has been generated to the fluorescence-image analyzing unit 65.

Here, the fluorescence-image correcting unit 66 divides the gradation values F of the fluorescence image G2 by the gradation values of the R component of the white-light image G1 for the individual pixels to calculate the gradation values F' of the corrected fluorescence image G2' based on equation (15) below. In equation (15), $N_{FR}$ is a value defined by equation (16) below and represents the maximum value among the quotients obtained by dividing the gradation values F by the gradation values R.

[Eq. 15]

$$F' = 4095 \times \frac{1}{N_{FR}} \times \frac{F}{R}$$
(15)

[Eq. 16]

$$N_{FR} = \mathrm{Max}\left[\frac{F}{R}\right]$$
(16)

The fluorescence-image analyzing unit 65 calculates the average m' and standard deviation σ' of the gradation values F' by using the corrected fluorescence image G2' instead of the fluorescence image G2.

The condition setting unit 63 calculates the thresholds $S_R$, $S_G$, and $S_B$ based on equations (11) and (12) by using the average m' and standard deviation σ' instead of the average m and standard deviation σ.

The combining unit 64 calculates the gradation values R', G', and B' of the individual pixels of the individual color component images of the combined image G3 based on equation (17) below instead of equation (1), i.e., by using the corrected fluorescence image G2' instead of the fluorescence image G2.

[Eq. 17]

$$R' = R + r(F' - S_R)$$
$$G' = G + g(F' - S_G)$$
$$B' = B + b(F' - S_B)$$
(17)

Next, the operation of the thus-configured fluorescence observation apparatus 200 will be described.

Figure 7:
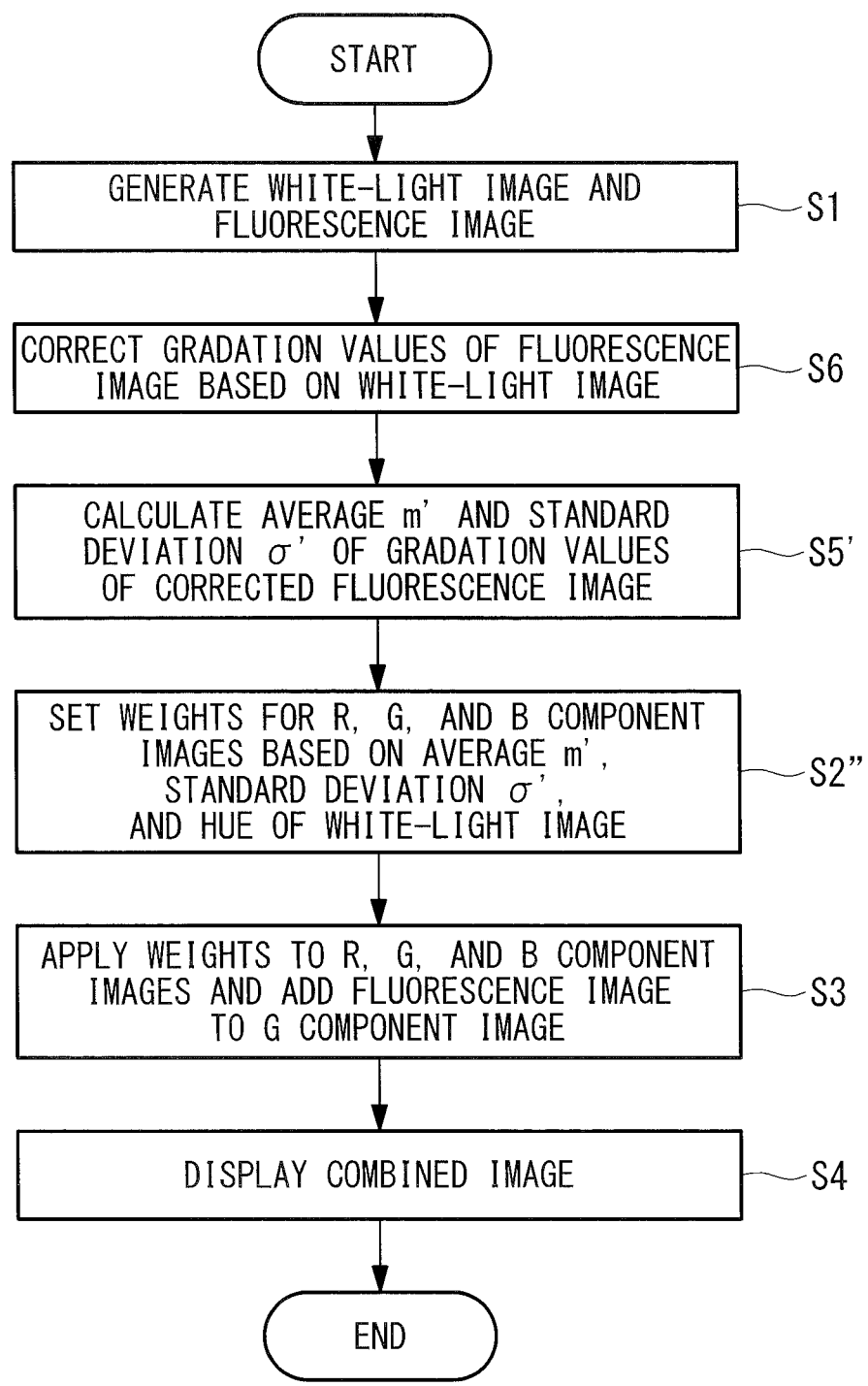
FIG. 7 is a flowchart for explaining processing executed by an image processing unit shown in FIG. 6.

With the fluorescence observation apparatus 200 according to this embodiment, processing is executed in the same manner as in the first embodiment until the generation of the white-light image G1 and the fluorescence image G2 (step S1). The generated white-light image G1 and fluorescence image G2 are forwarded to the fluorescence-image correcting unit 66. In the fluorescence-image correcting unit 66, as shown in FIG. 7, the fluorescence image G2 is divided by the white-light image G1 to generate the corrected fluorescence image G2' (step S6). Then, the fluorescence-image analyzing unit 65 calculates the distribution of the gradation values F' of the corrected fluorescence image G2' and calculates the average m' and standard deviation σ' of the gradation values F' from the distribution (step S5'). Then, the condition setting unit 63 sets the thresholds $S_R$, $S_G$, and $S_B$ by using the average m' and standard deviation σ', similarly to step S2' in the second embodiment (step S2'').

As described above, according to this embodiment, in the fluorescence-image analyzing unit 65 and the combining unit 64, the corrected fluorescence image G2' is used instead of the fluorescence image G2. The corrected fluorescence image G2', in which the gradation values are normalized by using the white-light image G1, is an image in which variations in the gradation values depending on variations in observation conditions, such as the observation distance and observation angle, have been removed so that the true intensities of fluorescence emitted from the individual positions of the object X are reflected more accurately. By using the corrected fluorescence image G2' described above, it is possible to display the fluorescence region Y in the combined image G3 such that the fluorescence region Y more accurately reflects the fluorescence-emitting region of the object X and the intensity of the fluorescence.

Fourth Embodiment

Next, a fluorescence observation apparatus 300 according to a fourth embodiment of the present invention will be described.

Figure 8:
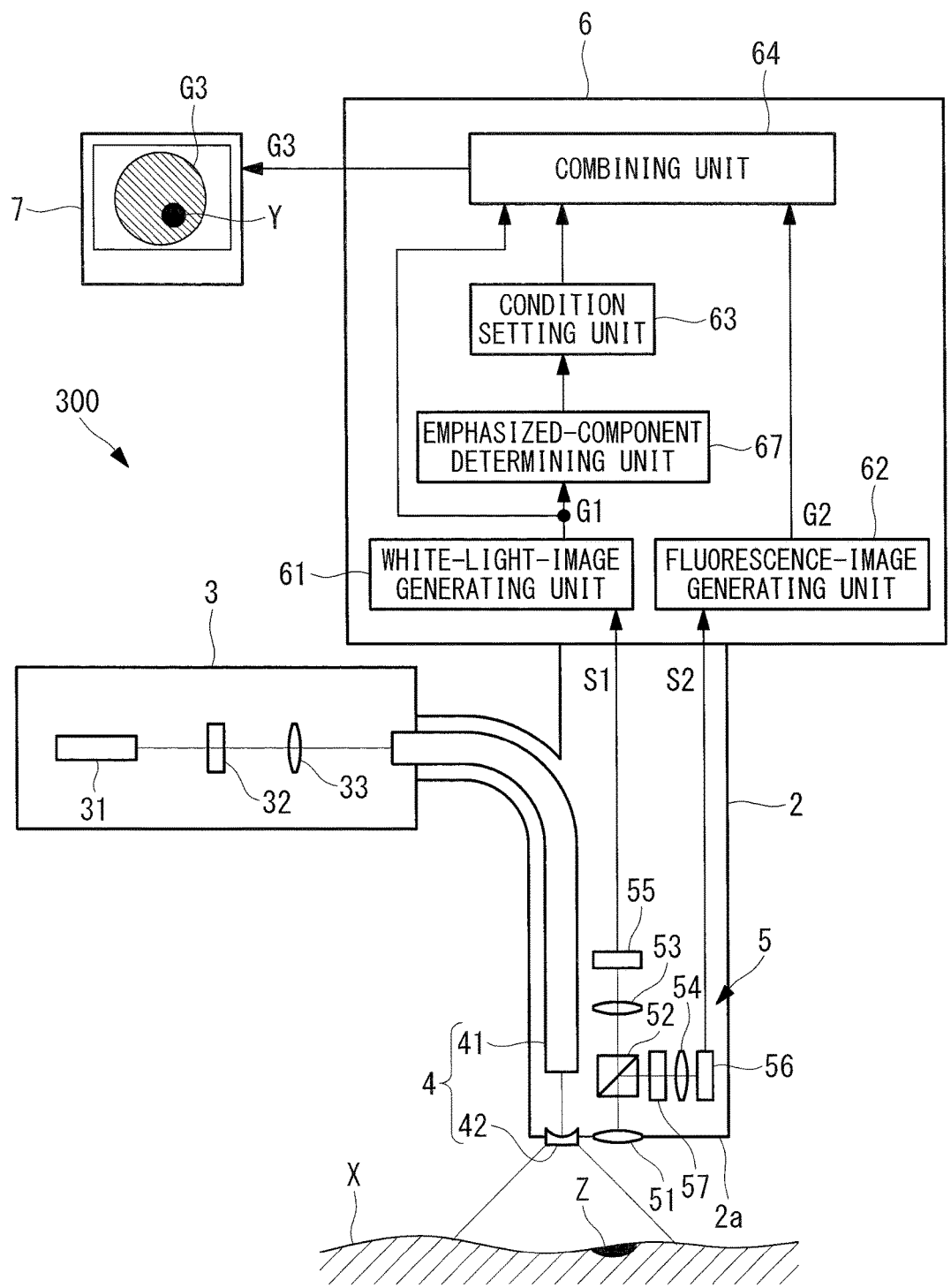
FIG. 8 is a diagram showing the overall configuration of a fluorescence observation apparatus according to a fourth embodiment of the present invention.

As shown in FIG. 8, the fluorescence observation apparatus 300 according to this embodiment differs from the first to third embodiments mainly in that the image processing unit 6 further includes an emphasized-component determining unit 67 that determines which of the R, G, and B components is to be emphasized, i.e., to which color component a greater weight is to be applied, and in that the condition setting unit 63 sets the coefficients r, g, and b and the thresholds $S_R$, $S_B$, and $S_G$ based on the result of determination by the emphasized-component determining unit 67. Thus, regarding this embodiment, the description will be directed mainly to the emphasized-component determining unit 67, the fluorescence-image correcting unit 66, and the fluorescence-image analyzing unit 65, and parts common to those in the first and second embodiments will not be described.

The emphasized-component determining unit 67 is implemented by the computer or the dedicated hardware.

For each of the pixels of the white-light image G1, the emphasized-component determining unit 67 determines the color component to be emphasized based on the color components of the pixel and outputs the result of determination for the pixel to the condition setting unit 63. For example, in the case where the gradation value of the G component of the white-light image G1 is greater than or equal to a predetermined threshold, the emphasized-component determining unit 67 sets the G component to be an emphasized component and the R component and B component to be non-emphasized components. In the case where the gradation value of the G component of the white-light image G1 is less than the predetermined threshold, the emphasized-component determining unit 67 sets the B component to be an emphasized component and the R component and G component to be non-emphasized components.

The condition setting unit 63 sets the coefficients r, g, and b and the thresholds $S_R$, $S_B$, and $S_G$ such that the weight for the emphasized component determined by the emphasized-component determining unit 67 becomes greater than the weights for the non-emphasized components. For example, the condition setting unit 63 uses equation (2) for a pixel with which the emphasized component is the G component, uses an equation obtained by exchanging R and G in equation (2) for a pixel with which the emphasized component is the R component, and uses an equation obtained by exchanging B and G in equation (2) for a pixel with which the emphasized component is the B component, and sets the coefficients r, g, and b and the thresholds $S_R$, $S_B$, and $S_G$ for each of the pixels.

According to this embodiment, in the case where the G component of the white-light image G1 is greater than or equal to the predetermined threshold, it is possible to generate a combined image G3 with good visibility of the fluorescence region Y by using the G component as an emphasized component. On the other hand, in the case where the G component is less than the threshold, since the gradation value of the G component is small, it is possible to generate a combined image G3 in which the visibility of the fluorescence region Y is further improved by choosing a component other than the G component (B component or R component) as an emphasized component. As described above, it is possible to choose and determine the emphasized component more appropriately in accordance with the color components at each position of the white-light image G1. This makes it possible to improve the visibility of the fluorescence region Y in the combined image G3.

Although the emphasized-component determining unit 67 determines an emphasized component and non-emphasized component based on the magnitude of the G component in this embodiment, alternatively, the emphasized-component determining unit 67 may determine an emphasized component and non-emphasized component based on the ratio of two color components, for example, the ratio between the G component and the B component.

Furthermore, although the first to fourth embodiments have been described above in the context of examples where the fluorescence image G2 is assigned to the G component image in generating the combined image G3, the color component image to which the fluorescence image G2 is assigned can be changed as required. That is, the fluorescence image G2 may be assigned to the R component image or the B component image, and the fluorescence image G2 may be divided and assigned to multiple component images.

For example, in the case of the first embodiment, equation (2) may be modified into equation (18) below.

In this case, a combined image G3 is generated from an R component image and a G component image to which negative weights have been applied and a B component image to which a positive weight has been applied. Thus, it is possible to emphasize the B component, in which the fluorescence region Y is displayed, relative to the R component and G component in the fluorescence region Y of the combined image G3.

[Eq. 18]

$$S_R = 1000 + 1000 \times \frac{4095 - R}{4095}$$
$$S_G = 1000 + 1000 \times \frac{4095 - G}{4095}$$
$$S_B = 1000 + 500 \times \frac{4095 - G}{4095} + 500 \times \frac{4095 - R}{4095}$$
$$r = -1 \times \frac{R}{4095}$$
$$g = -1 \times \frac{G}{4095}$$
$$b = 1 + 0.5 \times \frac{R}{4095} + 0.5 \times \frac{G}{4095}$$

(18)

Furthermore, the first to fourth embodiments described above may be embodied in arbitrary combinations as required.

Furthermore, although the dynamic range of each of the images G1, G2, G2' and G3 is assumed to be 12 bits in the first to fourth embodiments described above, the dynamic range is not limited to 12 bits and may be changed as required. For example, in the case where 16-bit images are used, 65535 is substituted for 4095 in each of equations (2) to (18).

Furthermore, the values (−1, 0.5, 1, 500, 1000) used in equations (2) to (18) given above are just examples and may be changed as required.

Furthermore, although the condition setting unit 63 continuously varies the weights that are applied to the individual color component images in the first to fourth embodiments described above, alternatively, the weights may be varied stepwise. For example, in the case of equation (2), the thresholds $S_R$ and $S_B$ may be defined as step functions of the gradation values R and B.

REFERENCE SIGNS LIST 1, 100, 200, 300 Fluorescence observation apparatuses
2 Inserted portion
3 Light source
4 Illumination unit
5 Image capturing unit
6 Image processing unit
7 Display unit
31 Xenon lamp
32 Filter
33 Coupling lens
41 Light guide fiber
42 Illumination optical system
51 Objective lens
52 Dichroic mirror
53, 54 Focusing lenses
55, 56 Image capturing elements
57 Excitation-light cutting filter
61 White-light-image generating unit
62 Fluorescence-image generating unit
63 Condition setting unit
64 Combining unit
65 Fluorescence-image analyzing unit
66 Fluorescence-image correcting unit
67 Emphasized-component determining unit
G1 White-light image
G2 Fluorescence image
G2' Corrected fluorescence image
G3 Combined image
X Object
Y Fluorescence region
Z Lesion

The invention claimed is:

1. A fluorescence observation apparatus comprising:
a light source configured to irradiate an object with white light and excitation light; and
a processor comprising hardware, wherein the processor is configured to implement:
a fluorescence-image generating unit configured to generate a fluorescence image based on captured fluorescence generated at the object due to irradiation with the excitation light from the light source;
a white-light-image generating unit configured to generate a white-light image, composed of multiple color component images, based on captured return light returned from the object due to irradiation with the white light from the light source;
a combining unit configured to add the fluorescence image to each of the multiple color component images and combine the multiple color component images to which the fluorescence image has been added to generate a combined image; and
a condition setting unit configured to set, based on the multiple color component images of the white light, weight for the fluorescence image which is added to each of the multiple color component images such that the weight for the fluorescence image which is added to at least one of the multiple color component images is greater than the weight for the fluorescence image which is added to the other of the multiple color component images and that the weight for the fluorescence image which is added to the at least one of the multiple color component images is set to be a greater value as gradation value of the other of the multiple color component images in the white-light image increase,
wherein the combining unit is configured to add the fluorescence image to which the weight, set by the condition setting unit, has been applied to each of the multiple color component images.

2. The fluorescence observation apparatus according to claim 1,
wherein the condition setting unit is configured to set a smaller value for the weight for the fluorescence image which is added to the other of the multiple color component images as gradation value of the other of the multiple color component images in the white-light image increase.

3. The fluorescence observation apparatus according to claim 1,
wherein the condition setting unit is configured to set the weight based on gradation values of the fluorescence image in addition to the multiple color component images of the white-light image, and sets a greater value for the weight for the fluorescence image which is added to the at least one of the multiple color component images as the gradation values of the fluorescence image increase.

4. The fluorescence observation apparatus according to claim 1,
wherein the condition setting unit is configured to set the weight based on gradation values of the fluorescence image in addition to the multiple color component images of the white-light image, and sets a smaller value for the weight for the fluorescence image which is added to the other of the multiple color component images as the gradation values of the fluorescence image increase.

5. The fluorescence observation apparatus according to claim 1,
wherein the combining unit is configured to apply the weight to only a region having gradation values greater than or equal to a predetermined threshold in the fluorescence image.

6. The fluorescence observation apparatus according to claim 5,
wherein the processor is further configured to implement a fluorescence-image analyzing unit configured to calculate an average of the gradation values of the fluorescence image and a standard deviation of the gradation values, wherein the condition setting unit is configured to set the predetermined threshold based a the sum of the average and standard deviation of the gradation values, calculated by the fluorescence-image analyzing unit.

7. The fluorescence observation apparatus according to claim 6,
wherein the processor is further configured to implement a fluorescence-image correcting unit configured to correct the gradation values of the fluorescence image by dividing the fluorescence image by the white-light image,
wherein the fluorescence-image analyzing unit is configured to calculate the average and standard deviation by using the fluorescence image that has been corrected by the fluorescence-image correcting unit.

8. The fluorescence observation apparatus according to claim 1,
wherein the processor is further configured to implement a fluorescence-image correcting unit configured to correct gradation values of the fluorescence image by dividing the fluorescence image by the white-light image,
wherein the combining unit and the condition setting unit use the fluorescence image that has been corrected by the fluorescence-image correcting unit as the fluorescence image.

9. The fluorescence observation apparatus according to claim 1,
wherein the processor is further configured to implement an emphasized-component determining unit configured to choose a color component image to which the fluorescence image is added in accordance with the multiple color component images of the white-light image.

10. A fluorescence observation apparatus comprising:
a light source configured to irradiate an object with white light and excitation light; and
a processor comprising hardware, wherein the processor is configured to implement:
a fluorescence-image generating unit configured to generate a fluorescence image based on captured fluorescence generated at the object due to irradiation with the excitation light from the light source;
a white-light-image generating unit configured to generate a color white-light image, composed of multiple color component images, based on captured return light returned from the object due to irradiation with the white light from the light source;
a combining unit configured to add the fluorescence image to each of multiple color component images and combine the multiple color component images to which the fluorescence image has been added to generate a combined image; and
a condition setting unit configured to set, based on the multiple color component images of the white light, weight for the fluorescence image which is added to each of the multiple color component images such that the weight for the fluorescence image which is added to at least one of the multiple color component images is greater than the weight for the fluorescence image which is added to the other of the multiple color component images and that the weight for the fluorescence image which is added to the other of the multiple color component images is set to be a smaller value as gradation value of the other of the multiple color component images in the white-light image increase,
wherein the combining unit is configured to add the fluorescence image to which the weight, set by the condition setting unit, has been applied to each of the multiple color component images.

11. The fluorescence observation apparatus according to claim 10,
wherein the condition setting unit is configured to set a greater value for the weight for the fluorescence image which is added to the at least one of the multiple color component images as the gradation value of the other of the multiple color component images in the white-light image increase.

12. A fluorescence observation apparatus comprising:
a light source configured to irradiate an object with white light and excitation light; and
a processor comprising hardware, wherein the processor is configured to implement:
a fluorescence-image generating unit configured to generate a fluorescence image based on captured fluorescence generated at the object due to irradiation with the excitation light from the light source;
a white-light-image generating unit configured to generate a color white-light image, composed of multiple color component images, based on captured return light returned from the object due to irradiation with the white light from the light source;
a combining unit configured to add the fluorescence image to each of multiple color component images and combine the multiple color component images to which the fluorescence image has been added to generate a combined image; and
a condition setting unit configured to set, based on the multiple color component images of the white light and gradation values of the fluorescence image, weight for the fluorescence image which is added to each of the multiple color component images such that the weight for the fluorescence image which is added to at least one of the multiple color component images is greater than the weight for the fluorescence image which is added to the other of the multiple color component images and that the weight for the fluorescence image which is added to the other of the multiple color component images is set to be a smaller value as the gradation values of the fluorescence image increase,
wherein the combining unit is configured to add the fluorescence image to which the weight, set by the condition setting unit, has been applied to each of the multiple color component images.

* * * * *